United States Patent [19]
Farzin-Nia et al.

[11] Patent Number: 5,984,679
[45] Date of Patent: Nov. 16, 1999

[54] METHOD OF MANUFACTURING SUPERELASTIC ENDODONTIC FILES AND FILES MADE THEREFROM

[75] Inventors: Farrokh Farzin-Nia, Inglewood; William Otsen, Glendora, both of Calif.

[73] Assignee: Ormco Corporation, Glendora, Calif.

[21] Appl. No.: 08/938,507

[22] Filed: Sep. 26, 1997

[51] Int. Cl.[6] .................................................. A61C 5/04
[52] U.S. Cl. .......................................................... 433/102
[58] Field of Search .............................. 433/81, 102, 224, 433/20

[56] References Cited

U.S. PATENT DOCUMENTS

| | | | |
|---|---|---|---|
| 4,443,193 | 4/1984 | Roane ...................................... | 433/102 |
| 5,044,947 | 9/1991 | Sachdeva et al. ......................... | 433/20 |
| 5,106,298 | 4/1992 | Heath et al. .............................. | 433/102 |
| 5,125,838 | 6/1992 | Seigneurin ............................... | 433/102 |
| 5,302,129 | 4/1994 | Heath et al. .............................. | 433/224 |
| 5,429,501 | 7/1995 | Farzin-Nia et al. ...................... | 433/21 |
| 5,464,362 | 11/1995 | Heath et al. .............................. | 451/48 |
| 5,527,205 | 6/1996 | Heath et al. .............................. | 451/48 |
| 5,628,674 | 5/1997 | Heath et al. .............................. | 451/48 |
| 5,655,950 | 8/1997 | Heath et al. .............................. | 451/48 |
| 5,752,825 | 5/1998 | Buchanan ............................. | 433/102 X |
| 5,762,541 | 6/1998 | Heath et al. ......................... | 433/102 X |
| 5,775,902 | 7/1998 | Matsutani et al. ...................... | 433/102 |

OTHER PUBLICATIONS

Harmeet Walia, et al., An Intial Investigation of the Bending and Torsional Properties of Nitinol Root Canal Files, Journal of Endodontics, vol. 14, No. 7, Jul. 1988.

*Primary Examiner*—Nicholas D. Lucchesi
*Attorney, Agent, or Firm*—Wood, Herron & Evans. L.L.P.

[57] ABSTRACT

A method of forming a superelastic endodontic file by grinding a superelastic wire to form a file blank, and rotating a first end of the blank while preventing rotation of a second end of the blank is disclosed. The file blank is maintained in the austenite phase until twisted to form a stress induced martensite which is plastically deformed by the twisting. A heat treatment step may be performed prior to twisting, during twisting or after twisting of the preform. The method disclosed allows for increased flexibility in the design of files including the production of a rhomboid superelastic file.

61 Claims, 3 Drawing Sheets

METHOD OF MANUFACTURING SUPERELASTIC ENDODONTIC FILES AND FILES MADE THEREFROM

BACKGROUND OF THE INVENTION

Previously known endodontic root canal files have been primarily made from carbon steel or stainless steel wire blanks which are ground to a desired size, taper and cross-sectional shape (for example, square, triangular or rhomboid). The wire blank is gripped on a first end while spring-loaded jaws secure the ground portion of the blank. The blank is then rotated from the gripped end while the jaws are moved axially away from that end. The jaws which secure the ground portion move along the ground wire blank, but do not allow the distal end of the blank to twist, thereby forming a twisted portion and helical flutes from the edges of the blank between the gripped end and the jaws. The cross-sectional shape, size and taper as well as the speed of twisting and spring force may be controlled to attain the desired properties in the final product. One such endodontic instrument is shown in U.S. Pat. No. 4,443,193, herein incorporated in its entirety by reference.

With the introduction of superelastic materials such as nickel titanium alloys, it has been recognized that superelastic endodontic files would provide more elastic flexibility in bending and torsion than the previous steel files. The paper, *An Initial Investigation of the Bending and Torsional Properties of Nitinol Root Canal Files*, Walia et al., *Journal of Endodontics*, Volume XIV, No. 7, July 1988, studied the feasibility of manufacturing superelastic nickel titanium root canal files and evaluated the bending and torsional properties of these instruments. In order to fabricate nickel titanium files the Walia article discloses the machining of the fluted structure of a K-type file directly on cylindrical wire blanks.

U.S. Pat. Nos. 5,464,362, 5,527,205 and 5,628,674 disclose the machining process used to grind the files disclosed in the Walia et al. article in which the fluted structure of the K-type file is ground directly on a cylindrical nickel titanium wire blank to create cutting edges at the apices. U.S. Pat. No. 5,464,362 provides a cylindrical rod of superelastic material having a diameter between 0.0024" and 0.062" which is translated axially, relative to a rotating grinding wheel, at an axial feed rate of between about 3 inches per minute and 8 inches per minute, with the preferred rate being not more than about 5 inches per minute. The rod is rotated about its longitudinal axis while it is translated relative to the wheel so that the wheel removes at least about 25% of the diameter of the rod at the point of maximum removal and forms at least one helical flute in the rod. In order to accomplish this grinding, the wheel is rotated at a surface speed of not more than about 3,000 surface feet per minute and preferably not more than about 2,200 surface feet per minute. The grinding wheel also has a grit size greater than about 200 grit and preferably greater than about 220 grit. If the file of the U.S. Pat. No. 5,464,362 is to have more than one helical flute, a first flute is ground, the rod is indexed about its longitudinal axis either by 180° (two flutes), or 120° (three flutes), and the grinding step is repeated.

SUMMARY OF THE INVENTION

In order to provide an endodontic file with a low modulus of elasticity which is more flexible in bending and torsion than conventional steel files and to overcome the problems with grinding disclosed in the Walia article and which the U.S. Pat. Nos. 5,464,362, 5,527,205 and 5,628,674 continue to have, a preground superelastic blank of a predetermined cross-sectional shape is twisted to provide helical flutes. In order to maintain its shape the file is maintained in the austenite phase until twisted. To maintain the file preform in the austenite phase the file is maintained above the austenite finish temperature Af prior to and during twisting. The material of the file is converted from the austenite phase to the martensite phase by the stress applied in twisting. This stress induced martensite is plastically deformed during twisting so that the fluted profile is retained after the twisting process is performed. Due to the pregrinding of the file preform it is possible to fabricate a superelastic file having myriad transverse cross-sections, including a rhomboid cross-sections, from a superelastic material.

DETAILED DESCRIPTION OF THE INVENTION

Superelastic materials are alloys which return to their original shape after substantial deformation. Superelastic alloys such as nickel titanium (NiTi) can withstand several times more strain than conventional materials, such as stainless steel, without becoming plastically deformed. Further, a superelastic material will generally recover approximately 6% after twisting at ambient temperature while a stainless steel will recover only 1–2% after twisting. Typically, superelastic alloys undergo a stress induced martensitic transformation which allows for shape memory properties. Shape memory and superelasticity are found in stoichiometric NiTi, near-equiatomic Ni—Ti, for example, 50.8 atomic percent Ti and 49.2 atomic percent Ni, Ni—Ti—Cu, Ni—Ti—Nb and Ni—Ti—Fe alloys as well as beta-phase titanium or other Ti based alloys. Examples of suitable nickel-titanium alloys in various stoichiometric ratios are disclosed in U.S. Pat. No. 5,044,947 (nickel-titanium-copper alloy) and U.S. patent application Ser. Nos. 08/221,638 and 08/454,016, inventor Sachdeva et al., entitled "NiTiNb Alloy Processing Method and Articles Formed Thereby" (nickel-titanium-niobium-alloy). The disclosures of U.S. Pat. No. 5,044,947 and the aforesaid applications are hereby incorporated by reference.

The specific alloy composition is not critical to the present invention; other materials which exhibit superelastic effects may be used. For example U.S. Pat. No. 5,429,501, herein incorporated in its entirety by reference, discloses superelastic and shape memory beta-phase titanium. To form beta-phase titanium, metallic titanium may be alloyed with molybdenum, chromium, zirconium, tin, vanadium, iron or niobium. Other compositions such as Cu—Zn alloys are also known to be superelastic and are suitable for use in the present invention. Another material suitable for use in the present invention is a work hardened nickel titanium having a martensitic crystal structure, such as that sold under the tradename NITANOL for orthodontic wires by Unitek Corp., Arcadia, Calif.

Figure 6:
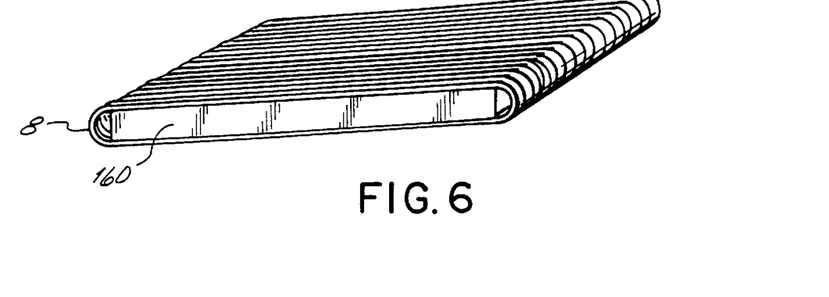
FIG. 6 is a perspective view of the apparatus used in straightening of the superelastic wire.

Superelastic materials have a temperature range in which the material may be permanently deformed. This range is known as the working temperature range Tw. When a superelastic wire is heated to a temperature in the working temperature range Tw, the wire may be permanently deformed so that when the wire is cooled, the deformed shape is maintained. Typically, the superelastic wire is packaged in coils and should be straightened prior to grinding and twisting. One method of straightening the wire 8 is to wrap the wire around a mandrel 160 as shown in FIG. 6. The mandrel 160 is then placed in a furnace and the wire 8 is heated into the Tw. The wire 8 is then cooled, removed from the mandrel and the curved ends are trimmed.

Superelastic alloys, when in the martensitic state (i.e., below the austenitic transformation temperature Af, the temperature at which the material is about 100% austenite), retain their deformed shape when subjected to stress. However the shape memory property returns the deformed material to its original predeformation configuration when heated above Af. In the present invention it is preferred to use an alloy having an Af temperature lower than about 37° C. (body temperature) so that the file will be in the austenitic phase during use in the body.

When the superelastic material is twisted, the material may form a stress induced martensite phase since less energy is necessary to stress induce and deform martensite than to deform austenite. If the file preform is deformed at room temperature and there is not enough strain to induce plastic deformation of the martensite phase, the wire will spring back to its original shape once the twisting force is released. It is also possible to permanently deform superelastic material by heating within the Tw range prior to and during twisting. Another method of permanently deforming a preform is by performing a rapid twist step to heat the superelastic material by internal friction to a temperature at which the material does form a stress induced martensite.

As used herein, the terms shape-memory alloy and superelastic alloy are intended to include all suitable alloy compositions which possess shape-memory and/or superelastic properties, respectively. Moreover, the term superelastic is intended to mean the ability of a material to withstand at least twice as much strain as stainless steel materials can withstand without plastic deformation. The term shape memory is intended to mean the ability of a wire to recover to its original state by the use of temperature. The term rhombus or rhomboidal is intended to define a geometric shape, having four major sides, which is substantially a parallelogram, i.e., including four equal sides and no internal right angles.

Figures 1, 1A, 1B:
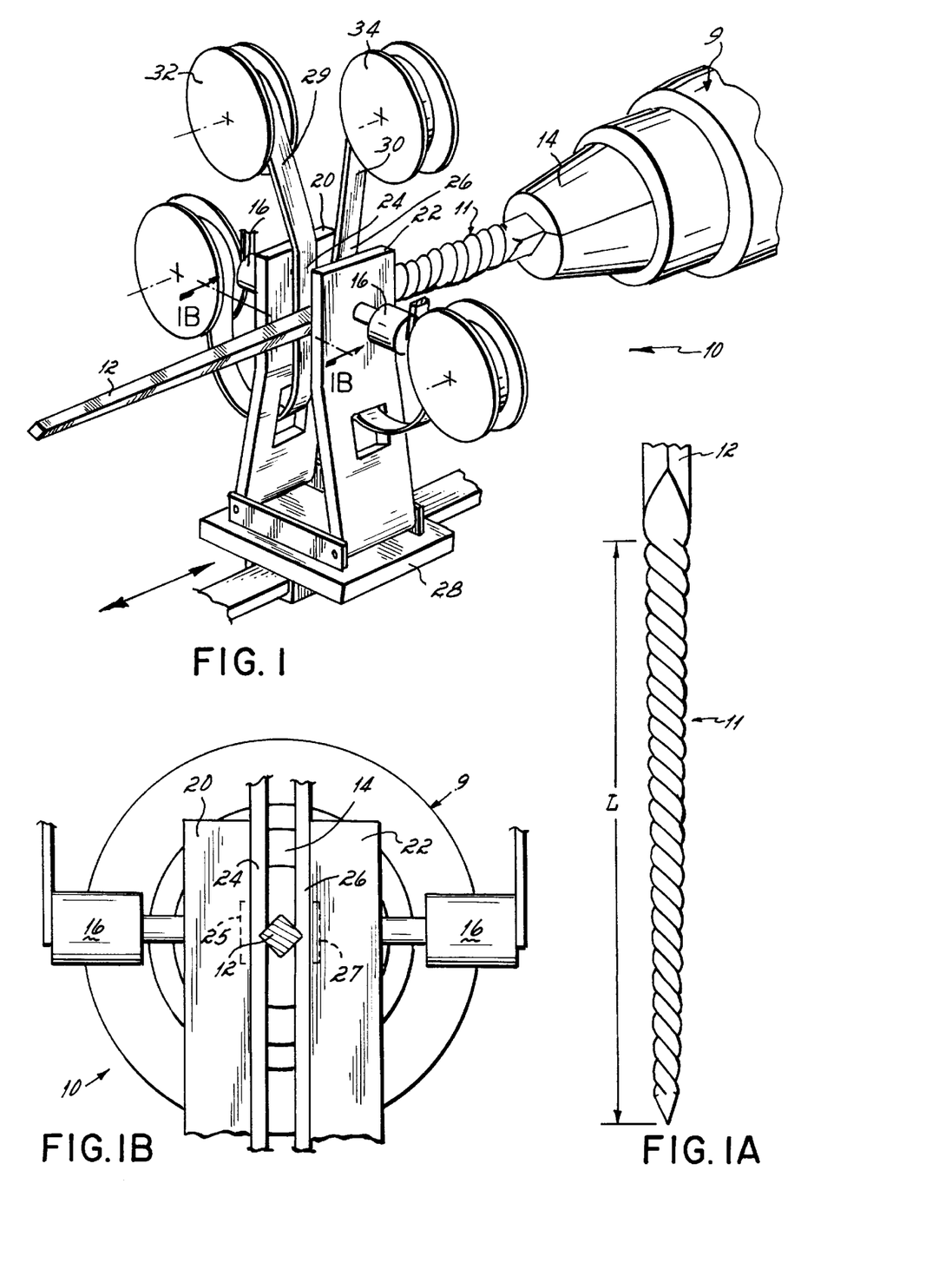
FIG. 1 is a schematic perspective view of one type of apparatus used in fabricating the file of the present invention.
FIG. 1A is a side view of a file formed on the apparatus of FIG. 1.
FIG. 1B is an enlarged cross-sectional view taken on line 1B—1B of FIG. 1A.

The files and file-forming processes of this invention are implemented, in preferred embodiments, with the apparatus 10 depicted in FIG. 1. Prior to twisting, file preforms are ground to the desired shape, including: length, transverse cross-section and taper, on any one of the devices shown in FIG. 2, 3, or 5.

Figure 2:
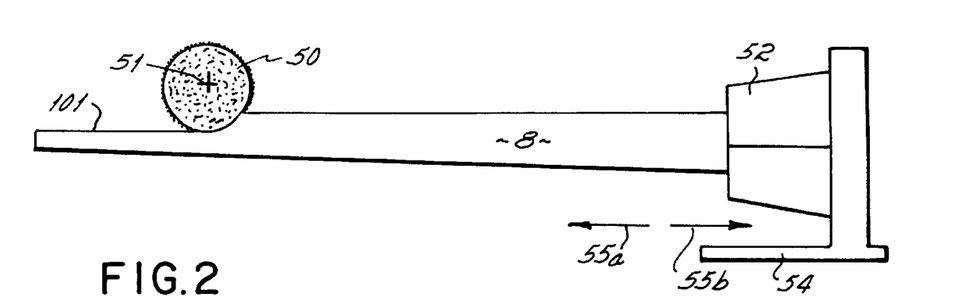
FIG. 2 is a schematic side view of one apparatus for forming a flat surface along the length of a file blank.

Cylindrical superelastic wires 8 are ground to form file preforms 12 which are subsequently twisted to form helically fluted files 11. The cylindrical rod 8 is mounted into collet 52 which is fixedly mounted upon a stage 54 which is selectively horizontally movable in opposite directions as designated by arrows 55a and 55b. Once rod 8 is mounted in the collet 52, grinding wheel 50 is lowered into contact with the rod 8. Stage 54 is then advanced horizontally rightwardly, as is seen in FIG. 2, to move collet 52 and rod 8 axially so that a flat surface 101 is ground on one side of the rod 8. After one such flat, that is, flat surface, has been ground along the working length L (see FIG. 1A) of the rod, grinding wheel 50 is lifted vertically, and stage 54 is moved axially leftwardly to the initial or home position so that the grinding wheel 50 is aligned with the upper portion of the inner end of the working length of the partially ground rod. Collet 52 is then indexed about its central axis by a predetermined angle, the magnitude of which depends on the number of flutes desired in the finished file. Indexing rotational angles of 180°, 120° and 90° are employed for 2, 3 and 4 flute files, respectively. It is also possible to rotate the collet by a series of angles (e.g. 60°, 120°, 60°) to obtain a file preform having a rhomboidal cross section. Grinding wheel 50 is then lowered to the desired depth of contact with the rod 8, and stage 54 is then moved rightwardly to move rod 8 axially past grinding wheel 50 to grind the second flat surface on the file blank. The foregoing process is repeated until all the flats have been ground on the file blank.

Figure 2A:
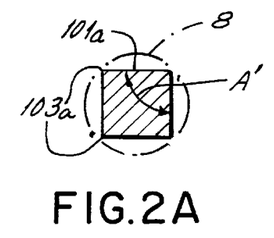
FIGS. 2A, 2B, 2C and 2D are transverse cross-sectional views, perpendicular to the longitudinal axis of the finished file or the file blank using the apparatus of FIG. 2 or FIG. 6.
Figure 2B:
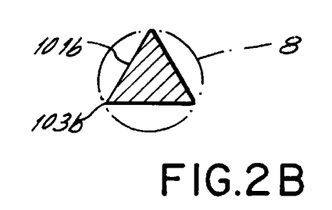
Figure 2C:
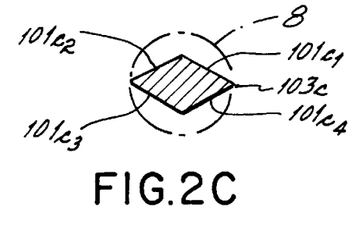

As noted, by varying the angle which collet 52 indexes rod 8, it is possible to form file blanks having three or more apices 103 shown generally in FIGS. 2A–2C. The apices 103 of the preground file blank, once twisted, and permanently helically fluted, form the cutting edges of the helically fluted file. Typically, files include three or four apices or helical cutting edges 103.

Figure 2D:
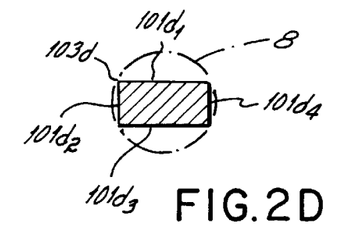

In order to form a file blank having a square transverse cross section as shown in FIG. 2A, rod 8 is indexed 90° after each flat surface 101 is ground. In order to form a file blank having three apices and a triangular transverse cross section, the rod is indexed 120° after each flat surface is formed (as shown in FIG. 2B). Using the method of the present invention it is also possible to form a file having a rhomboidal transverse cross section (FIG. 2C). This is accomplished by grinding a first flat surface 101C$_1$; indexing the rod 60° clockwise as viewed in FIG. 2C and grinding a second flat surface 101C$_2$; indexing the rod 120° clockwise as viewed in FIG. 2C and grinding a third flat surface 101C$_3$; and indexing the rod 60° clockwise as viewed in FIG. 2C and grinding the fourth flat surface 101C$_4$. It is not necessary to change the initial depth of cut of the wheel to fabricate the square, triangular and rhomboidal preforms shown in FIGS. 2A–2C, respectively. However, in order to fabricate a preform having a rectangular cross-section, as shown in FIG. 2D, the initial depth of cut may be adjusted prior to forming each flat side or may be adjusted after opposing pairs of edges are ground. For example, as seen in FIG. 2D, a first flat side 101d$_1$, is ground; the rod 8 is then indexed 90°, the initial depth of cut reduced and a second flat side 101d$_2$ is ground; rod 8 is then indexed 90°, the initial depth of cut is increased to the depth used for the cut of side 101d$_1$, and a third flat side 101d$_3$ is ground; rod 8 is then indexed 90°, the initial depth of cut is reduced to the depth used for the cut of side 101d$_2$ and fourth side 101d$_4$ is ground. It is also possible to grind flat side 101d$_1$, index the rod 180°, and grind flat side $101d_4$; index the rod 90° and decrease the initial depth of cut and grind flat side $101d_2$; and finally index the rod 180° and grinding the final flat side $101d_3$.

Figure 3:
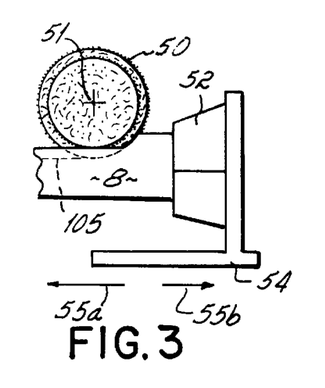
FIG. 3 is a schematic side view of an apparatus similar to FIG. 2 for forming a concave surface along the length of a file blank.
Figure 3A:
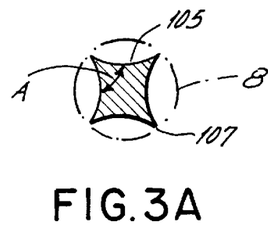
FIGS. 3A, 3B and 3C are transverse cross-sectional views, perpendicular to the longitudinal axis of the finished file or the file blank, showing concave surfaces formed on file blanks, using the apparatus of FIG. 3.
Figure 3B:
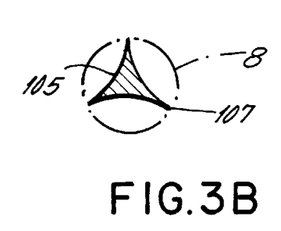
Figure 3C:
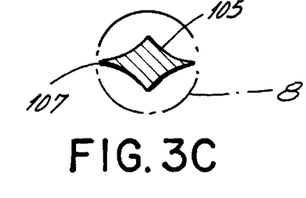

It is possible to form a variety of different cross sectional shapes by varying the surface of the grinding wheel and/or the index angles. For example, by dressing the surface of grinding wheel 50 so that the surface is convexed, as shown in FIG. 3, it is possible to form ground surfaces 105 having the concave shapes shown in FIGS. 3A, 3B and 3C, rather than the flat shapes of the surfaces 101 shown in FIGS. 2A, 2B and 2C. When the surface of the grinding wheel 50 is convexed, the angle A of the apices 107 (FIG. 3A) is more acute for a file having the same index angle and number of sides than is angle A' of the apices 103 (FIG. 2A) when the surface of the grinding wheel 50 is flat (FIG. 2). While angle A is more acute and provides a sharper cutting edge, that edge is weaker due to the lower amount of material at the apex. Thus, the apices shown in FIGS. 2A–2C are more rugged to maintain a usable edge and provide for a longer working life.

Figures 4, 5:
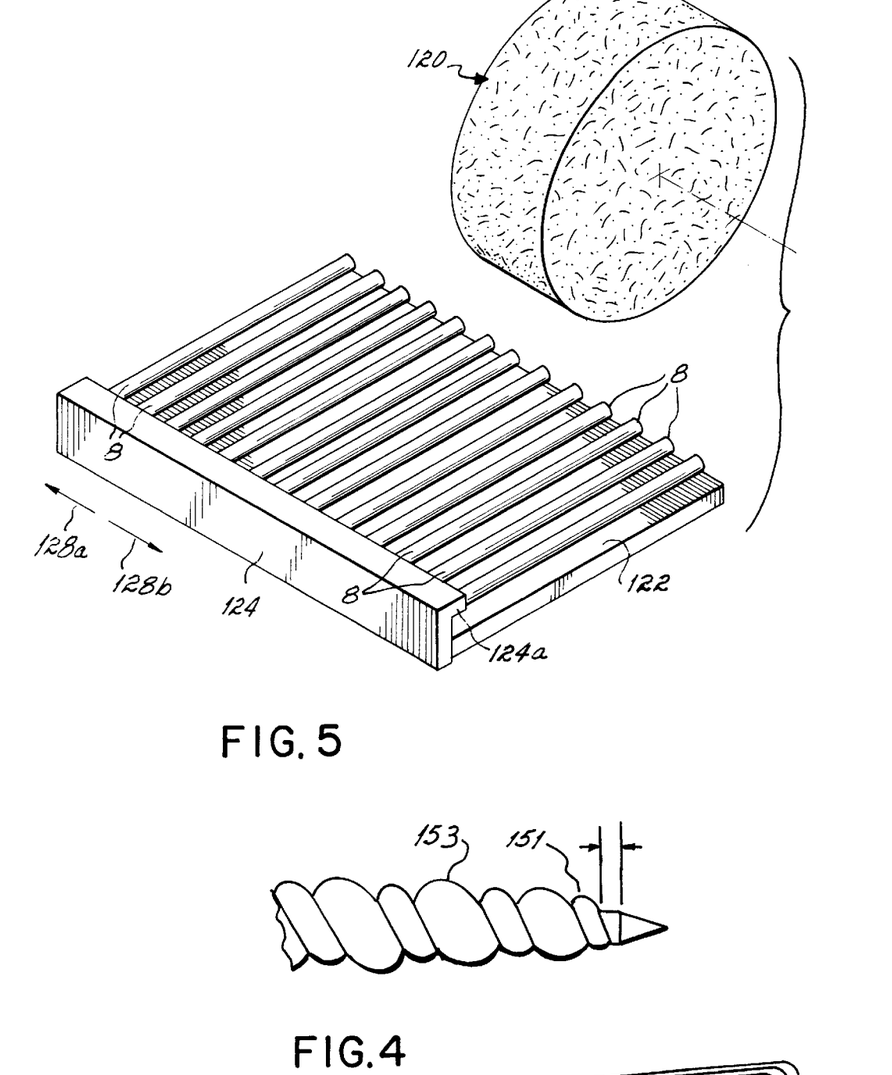
FIG. 4 is a detail view of a rhomboidal file tip.
FIG. 5 is a perspective view of another apparatus for forming flat surfaces along the length of a number of file blanks.

Another device for grinding cylindrical rods 8 is shown in FIG. 5. FIG. 5 shows a wide grinding wheel 120 which moves transversely to the longitudinal axes of a large number of rods 8 to grind a flat surface onto the rods. The cylindrical rods 8 are placed upon rest 122. The rods 8 are disposed in parallel and extend along substantially the entire width of the rest 122. The parallel rods 8 are held by retainer 124 which is movable along the length of rest 122 as shown by opposing arrows 128a and 128b. Movable retainer 124 includes lateral projection 124a which extends over an end portion of rods 8 to secure the rods to rest 122 and prevent the rotation of the rods during grinding. Once rods 8 are retained between the lateral projection 124a and the rest 122, grinding wheel 120 moves back and forth across the width of rest 122 to grind a flat surface on the entire working length of each rod 8. Typically, the grinding 120 wheel moves across each rod twice, once while traveling away from projection 124a and once while traveling toward projection 124a. During grinding, the wheel 120 may be moved straight across the rods or may move in a figure eight or zigzag pattern. The grinding wheel is preferably a porous wheel such as an ANSI standard C-601V wheel rotating at rate between 3,000 and 8,000 surface feet per minute and preferably about 5,000 surface feet per minute. The material is passed under the wheel at a feed rate between about 50 and 100 lineal feet per minute, and preferably about 75 lineal feet per minute.

After grinding a first flat side, the movable retainers 124 is translated with respect to the rest 122. The lateral projection 124a of the retainers 124 remains in contact with rods 8 so that the movement of the retainer along the direction shown by arrows 128a, 128b causes each rod to rotate by a predetermined angle about the longitudinal axis of the rods 8. Once the rotation is complete, a second flat surface is ground across the working length of the rod. Depending upon the desired cross section of the file 11, the rods 8 are typically rotated and ground one or more times.

After the file blanks have been ground to the desired cross-sectional file preform shape they are preferably heated to a temperature above ambient temperature prior to, during and subsequent to the twisting operation using thermal or frictional energy or a combination thereof. This temperature can be as high as the working temperature range Tw of the material of which they are formed.

The heating process may externally heat the wire preform in the collet 14 by the provision of induction coils, radiant heating elements or electrodes to provide for joulian heating. The temperature to which the preform is heated is based upon the specific alloy used. Alternatively, the files can be heated without the application of heat from an external heat source by twisting rapidly so that internal friction heats the file.

Once the file preforms are formed, they are twisted or heated and twisted on a device such as that shown in FIG. 1. The twisting apparatus 10, shown in FIG. 1, includes a drive head 9 which rotates about a horizontal axis. Extending from the drive head 9 is a collet 14 which circumferentially grips and secures the proximal or inner end of a preformed ground file blank 12 for rotation about the longitudinal axis thereof. The distal or outer end portion of the file blank 12 is secured by opposing jaws 20, 22, which are mounted on a stage 28 which moves parallel to the longitudinal axis of the file blank (horizontally as shown in FIG. 1), away from collet 14 at a predetermined rate as the collet rotates to twist the file blank 12. At least one of the jaws includes a spring or air cylinder 16 so that it may be compressed against the opposing jaw with a constant force. Each jaw includes a protectant layer 24, 26 which is malleable and able to withstand the working temperature of the file blank 12. Brass is one material known to be suitable. With each subsequent file formed, the jaws 20, 22 are provided with a new protectant layer 24, 26 from strips 29, 30 from a source 32, 34 such as take-off reels. The protectant layer may optionally be contacted by a heating element 25, 27 which may heat by any suitable process, such as an electrical heating process of joulian, radiant or induction heating or may be supplied with a heated fluid such as steam or oil.

In order to optimize the superelastic properties of the finished file it is desirable, although not essential, to heat treat the twisted files. The heat treatment may be performed in any furnace with air circulation. The radiant heating elements or electrodes to provide for joulian heating can be used for the post twist heat treatment.

Typically the files are made in a variety of working lengths varying from 19–30 mm. The specific variables which are typically controlled in fabricating such files are set forth in the Tables 1 and 2. In Tables 1 and 2 the variables A and B represent the minimum thickness of the transverse cross section at 16.00 mm and 3.00 mm, respectively, from the tip. The variables C and D represent the maximum thickness of the transverse cross section at 16.00 mm and 3.00 mm, respectively, from the tip.

Table 1 describes the characteristics of a twisted rhomboidal file. In observing the longitudinal cross section of a rhomboidal file there are alternating large flutes 153, resulting from the major axis of the rhombus, and small flutes 151, resulting from the minor axis of the rhombus. In Table 1 the column entitled Tight Flute Limit includes two values. The first value is the minimum acceptable length of a small flute 151 resulting from the twisting of the minor axis of the rhombus. The second value is the minimum acceptable length of a large flute 153 resulting from the twisting of the major axis of the rhombus. Similarly, the column entitled Loose Flute Limit includes two values. The first value is the maximum acceptable length of a small flute 151 resulting from the twisting of the minor axis of the rhombus. The second value is the maximum acceptable length of a large flute 153 resulting from the twisting of the major axis of the rhombus. In Table 1 the column labeled T max represents the maximum acceptable length of the untwisted portion at the distal tip of the file. In Table 2 the value L is the length of the ground portion of the rod.

It will be appreciated that different alloy compositions will possess a different shape-memory characteristic, a different transformation temperature (Af), a different modulus of elasticity, and a different working temperature range Tw. It is within the skill of one in the art based upon the teachings of the present invention to adjust the heating, twisting and heat treating steps based upon the specific properties of the material used.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method as shown and described. This has been a description of the present invention, along with the preferred method of practicing the present invention as currently known. However, the invention itself should only be defined by the appended claims, wherein

We claim:

1. A method of forming an endodontic file having a longitudinal axis and a predetermined transverse cross-sectional shape, and having apices defining longitudinal edges along the working length of the file, the method comprising the steps of:

providing an elongated preformed file blank of superelastic material having a predetermined transverse cross-sectional shape, the blank having integral working length and handle sections;

twisting the preformed file blank about its longitudinal axis to permanently, helically deform said blank to convert said longitudinal edges into helically shaped cutting edges; and maintaining the preformed file blank in the austenite phase up until immediately prior to the twisting step.

2. The method of claim 1 wherein the material of the file transforms to martensite phase during the twisting step.

3. The method of claim 2 wherein the martensite phase is a stress induced martensite phase.

4. The method of claim 3 wherein the stress induced martensite phase material is plastically deformed during the twisting step.

5. The method of claim 1 wherein the step of providing the preformed file blank includes the step of grinding at least one elongated narrow surface along the exterior of the blank for a distance approximately equal to the working length section of the file.

6. The method of claim 5 wherein the predetermined cross-sectional shape of the preformed file blank along its working length has a cross section selected from the group consisting of three-sided and four-sided polygons.

7. The method of claim 6 wherein the predetermined cross-sectional shape is substantially rhomboidal.

8. The method of claim 5 further comprising the step of heating the preformed file blank to a temperature above the Af temperature of said superelastic material prior to twisting.

9. The method of claim 8 wherein the heating step is performed by an electrical heating process selected from the group consisting of radiant, joulian and induction heating.

10. The method of claim 5 further comprising the step of heating the preformed file blank to a temperature of about 200°–400° F. prior to twisting.

11. The method of claim 5 further comprising the step of heat treating the preformed file blank by heating to a temperature within the Tw range of said superelastic material subsequent to the twisting step.

12. The method of claim 11 wherein the heating step includes electrically heating the blank in a process selected from the group consisting of radiant, joulian and induction heating.

13. The method of claim 5 wherein the grinding step is performed using a rotary grinding wheel having a surface speed of between about 3,000 and 8,000 surface feet per minute.

14. The method of claim 13 wherein the surface of the grinding wheel is concave.

15. The method of claim 13 wherein the surface of the grinding wheel is convex.

16. The method of claim 5 wherein the grinding step includes the steps of:

supporting at least one of said file blanks;

fixing the blank at a predetermined position in relation to the grinding wheel;

grinding a first elongated narrow surface along the working length section of the blank;

indexing the blank about its longitudinal axis; and grinding another elongated narrow surface along the working length section of the blank.

17. The method of claim 16 wherein the indexing and grinding steps are repeated at least twice after formation of the first elongated narrow surface to form a preformed file blank having a substantially triangular cross section.

18. The method of claim 16 wherein the indexing and grinding steps are repeated at least three times after formation of the first elongated narrow surface to form a preformed file blank having a substantially quadrilateral cross section.

19. The method of claim 16 wherein the blank is indexed approximately 90° during each indexing step.

20. The method of claim 16 wherein the blank indexing steps alternatively index the blank 60° and 120° to form a preformed file blank having a substantially rhomboidal cross section.

21. The method of claim 16 wherein the grinding step is performed using a rotary grinding wheel having a surface speed of between about 3,000 and 8,000 surface feet per minute.

22. The method of claim 21 wherein the grinding step is performed using a rotary grinding wheel having a surface speed of about 5,000 surface feet per minute.

23. The method of claim 16 wherein the grinding step is performed using a rotary grinding wheel having a surface speed of between about 3,000 and 8,000 surface feet per minute and a material feed rate of between about 50 and 100 lineal feet per minute.

24. The method of claim 16 wherein the grinding step is performed using a rotary grinding wheel having a surface speed of about 5,000 surface feet per minute and a material feed rate of between about 50 and 100 lineal feet per minute.

25. The method of claim 24 wherein the material feed rate is about 75 lineal feet per minute.

26. The method of claim 1 further comprising the step of elevating the temperature of the preformed file blank to a temperature above the Af temperature of said superelastic material during twisting.

27. The method of claim 26 wherein the heating step includes electrically heating the blank in a process selected from the group consisting of radiant, joulian and induction heating.

28. The method of claim 26 wherein the heating step is caused by internal friction of twisting, without the application of heat from an external heat source.

29. A method of forming an endodontic appliance from a material exhibiting superelastic characteristics comprising the steps of:

grinding a rod exhibiting superelastic characteristics, having a first end and a second end and a working length therebetween, to form a preform having a predetermined length, cross-sectional shape and taper along the working length thereof, the cross-sectional shape having corners which define longitudinal edges along the working length of the appliance; and twisting the preform to permanently helically deform said preform and form helical shaped cutting edges from said longitudinal edges.

30. The method of claim 29 wherein the preform is maintained in the austenite phase until immediately prior to twisting.

31. The method of claim 29 wherein the preform is transformed to the martensite phase during twisting.

32. The method of claim 29 further comprising the step of heating the preform to a temperature above the Af temperature of said preform prior to twisting.

33. The method of claim 29 wherein the grinding step includes the steps of:

retaining at least one of said rods in a predetermined position with respect to a grinding wheel;

grinding a first elongate narrow surface along the working length of the rod; and alternatively indexing the rod about the longitudinal axis thereof and subsequently grinding another elongate narrow surface along the working length of the rod.

34. The method of claim 33 wherein the preform is maintained in the austenite phase until immediately prior to twisting.

35. The method of claim 33 wherein the preform is transformed to the martensite phase by twisting.

36. The method of claim 33 further comprising the step of heating the preform to a temperature above the Af temperature of said preform prior to twisting.

37. The method of claim 33 wherein the grinding step is performed using a rotary grinding wheel having a surface speed of between about 3,000 and 8,000 surface feet per minute.

38. The method of claim 33 wherein the grinding step is performed using a rotary grinding wheel having a surface speed of about 5,000 surface feet per minute.

39. The method of claim 33 wherein the grinding step is performed using a rotary grinding wheel having a surface speed of between about 3,000 and 8,000 surface feet per minute and a material feed rate of between about 50 and 100 lineal feet per minute.

40. The method of claim 33 wherein the grinding step is performed using a rotary grinding wheel having a surface speed of about 5,000 surface feet per minute and a material feed rate of between about 50 and 100 lineal feet per minute.

41. The method of claim 40 wherein the material feed rate is about 75 lineal feet per minute.

42. The method of claim 33 wherein the grinding step is performed with a rotatable grinding wheel having a surface which is convex.

43. The method of claim 33 wherein the grinding step is performed with a grinding wheel having surface which is concave.

44. The method of claim 33 wherein the rod is indexed and ground twice after formation of the first elongate narrow surface to form a preform having a substantially triangular cross section along the working length.

45. The method of claim 33 wherein the rod is indexed and ground three times after formation of the first elongate narrow surface to form a preform having a substantially quadrilateral cross section along the working length.

46. The method of claim 45 wherein the rod is alternatively indexed approximately 60° and approximately 120° to form a file having a substantially rhomboidal cross section.

47. The method of claim 33 wherein the rod is indexed approximately 90° after formation of each elongate narrow surface.

48. The method of claim 29 wherein the grinding step is performed upon a single rod retained in a rotatable collar.

49. The method of claim 29 wherein the grinding step is performed upon a plurality of said rods retained in side-by-side parallel relationship.

50. The method of claim 29 wherein a plurality of said rods are retained, in side-by-side parallel relationship, upon a rest by a movable retainer.

51. The method of claim 29 further comprising the step of:

heating the preform by an electrical heating process selected from the group consisting of radiant, joulian and induction heating.

52. The method of claim 29 further comprising the step of:

heating the preform by internal friction during the twisting step.

53. The method of claim 29 wherein the twisting step includes the steps of:

securing the first end of the file preform in a rotatable collet;

securing the working length of the preform at a position proximate to the collet in a slidable non-rotatable work holder at a predetermined distance from said collet;

rotating the collet and the portion of the file preform proximate the collet; and increasing the distance between said collet and said work holder.

54. The method of claim 53 wherein:

the rotating step is performed at a predetermined rotation rate;

the distance increasing step is performed at a predetermined axial speed; and controlling the rotation rate and the speed to form a file having a predetermined twist rate.

55. An endodontic appliance having a predetermined transverse cross-sectional shape, comprising:

integral working length and handle sections formed of material exhibiting superelasticity above an austenitic finish temperature Af with said working length having the predetermined transverse cross-sectional shape defining corners, said working length being twisted about its longitudinal axis to permanently form helical cutting edges at the corners thereof.

56. The appliance file of claim 55 wherein said material is selected from the group consisting of near-equiatomic Ni—Ti, Ni—Ti—Nb alloys, Ni—Ti—Fe alloys, Ni—Ti—Cu alloys, Ni—Ti—Nb alloys, beta-phase titanium and combinations thereof.

57. The appliance file of claim 55 wherein said material is at least about 40 atomic percent Ti.

58. The appliance file of claim 57 wherein said material is about 50.8 atomic percent Ti and about 49.2 atomic percent Ni.

59. The appliance file of claim 55 wherein said predetermined transverse cross-sectional shape is selected from three and four sided polygons.

60. The appliance file of claim 55 wherein said predetermined transverse cross-sectional shape is substantially rhomboidal.

61. The appliance file of claim 60 wherein said rhombus has angles of about 60°–120°–60°–120°.

* * * * *

UNITED STATES PATENT AND TRADEMARK OFFICE
CERTIFICATE OF CORRECTION

PATENT NO : 5,984,679
DATED : November 16, 1999
INVENTOR(S) : Farzin-Nia et al.

It is certified that error appears in the above-identified patent and that said Letters Patent are hereby corrected as shown below:

Claim 56, line 1 reads, "The appliance file," and should read–The appliance–.

Claim 57, line 1 reads, "The appliance file," and should read–The appliance–.

Claim 58, line 1 reads, "The appliance file," and should read–The appliance–.

Claim 59, line 1 reads, "The appliance file," and should read–The appliance–.

Claim 60, line 1 reads, "The appliance file," and should read–The appliance–.

Claim 61, line 1 reads, "The appliance file," and should read–The appliance–.

Signed and Sealed this

Fifteenth Day of May, 2001

Attest:

NICHOLAS P. GODICI

*Attesting Officer*  *Acting Director of the United States Patent and Trademark Office*